United States Patent [19]
Federici

[11] Patent Number: 5,533,896
[45] Date of Patent: Jul. 9, 1996

[54] ARTICULATING DEVICE WITH AUTOMATIC ADAPTATION

[76] Inventor: Edmondo Federici, Via G. Ciaralli 26, 00156 Rome, Italy

[21] Appl. No.: 182,193

[22] PCT Filed: Jul. 20, 1992

[86] PCT No.: PCT/IT92/00084

§ 371 Date: Jan. 28, 1994

§ 102(e) Date: Jan. 28, 1994

[87] PCT Pub. No.: WO93/25160

PCT Pub. Date: Dec. 23, 1993

[30] Foreign Application Priority Data

Jun. 17, 1992 [IT] Italy .................. RM92A0460

[51] Int. Cl.$^6$ ................................. A61C 11/00
[52] U.S. Cl. ............................... 433/64; 433/63
[58] Field of Search ................... 433/54, 57, 61, 433/62, 63, 64, 65, 66

[56] References Cited

U.S. PATENT DOCUMENTS

| | | | |
|---|---|---|---|
| 2,603,869 | 7/1952 | Björklund | 433/57 |
| 3,159,915 | 12/1964 | Beu et al. | 433/57 |
| 4,189,837 | 2/1980 | Stele | 433/57 |
| 4,443,191 | 4/1984 | Guitierrez | 433/56 |
| 5,020,993 | 6/1991 | Levandoski | 433/57 |
| 5,073,109 | 12/1991 | Hadary | 433/57 |

FOREIGN PATENT DOCUMENTS

| | | |
|---|---|---|
| 8906103 | 9/1989 | Germany. |
| 3918497 | 12/1990 | Germany. |

*Primary Examiner*—Cary E. O'Connor
*Attorney, Agent, or Firm*—Beveridge, DeGrandi, Weilacher & Young

[57] ABSTRACT

The articulating device according to the present invention is divided in three parts (1, 4 and 7) that integrate one with the others, and provides the insertion of the vertical branch (7) onto the lower branch (4) from front to back, so as to allow the registration of the condylar distance, one side after the other, without the encumbersome mechanism simulating the temple-mandible articulation of the opposite side.

16 Claims, 3 Drawing Sheets

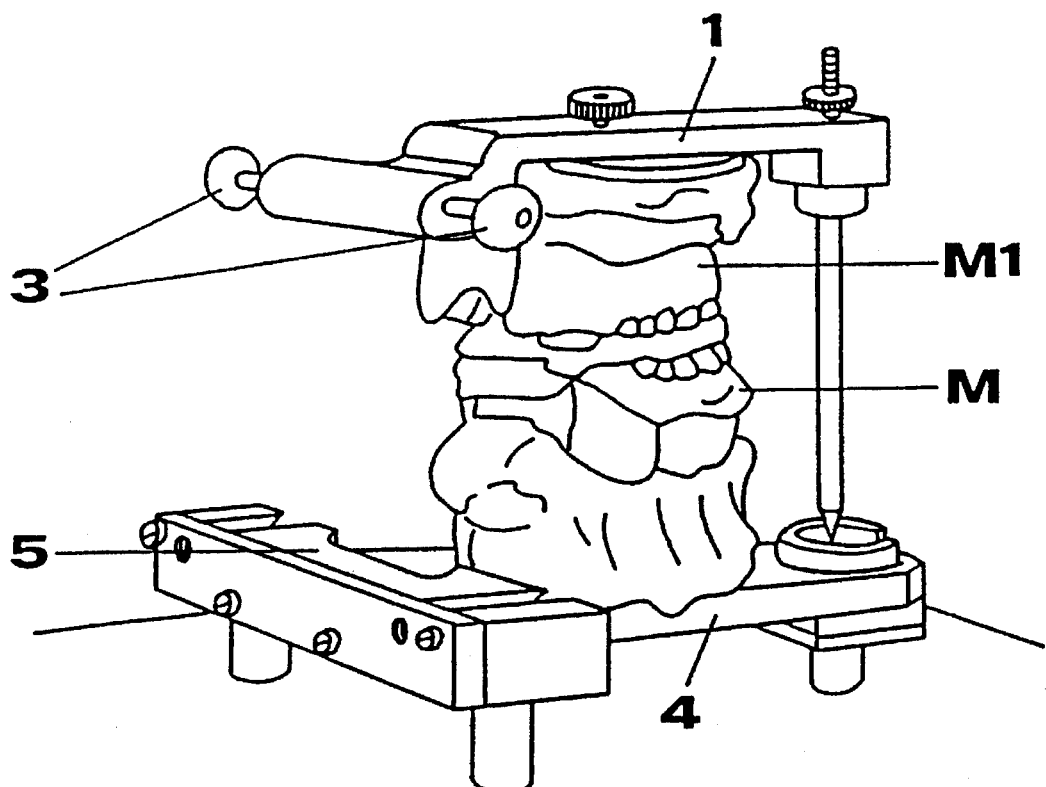
FIG. 3
FIG. 4
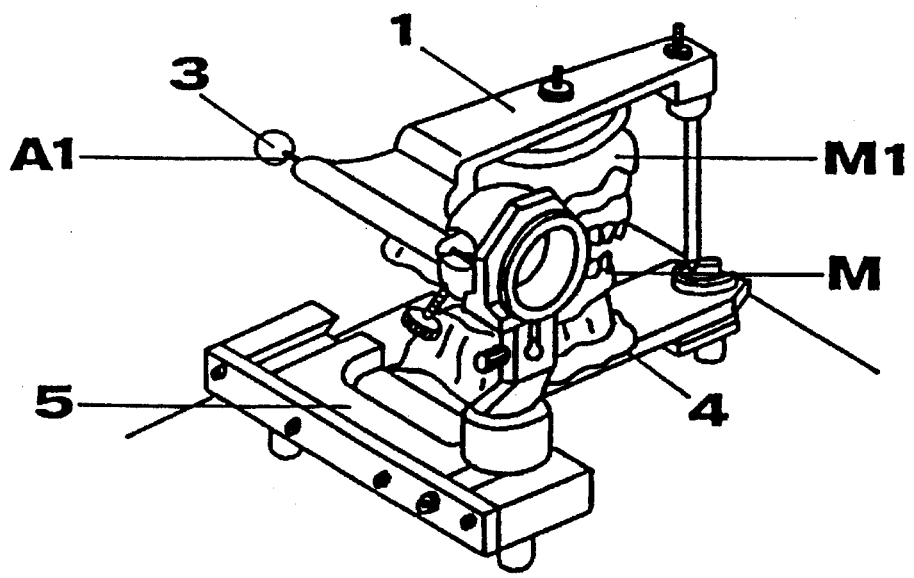

ARTICULATING DEVICE WITH AUTOMATIC ADAPTATION

BACKGROUND OF THE INVENTION

The present invention concerns an articulating device with automatic adaptation to the registered condyle distance.

It is already well known that an articulator is a subsidy for odontotechnicians, as it simulates the cranio-facial skeleton limited to the upper jaw, to the mandible and to the temple-mandible articulations.

The bone structure of the articulations consists of two fix elements, one for each side, inserted at the basis of the cranium, shown as glenoid cavities, and of two movable elements, the condyles, united one to the other by means of the mandible body.

The condyles get placed at the center of the relative glenoid cavities when the mouth is in an occlusion position, i.e. in the position of maximum intercuspidation.

When the mandible moves, the condyles inside the glenoid cavities move in synchrony; these movements are complex and tridimensional.

In the articulator, the upper branch shows the jaw, and the lower branch looks like a mandible, while the articulations have been transformed into mechanisms placed in part on the upper branch, in part on the lower branch.

The articulators may be divided in two kinds: those that have the condylar part in the lower branch and the glenoid part in the upper branch and are called ARCON, i.e. articulating condyles, and those non-ARCON, that have the condyles in the upper branch and in the lower branch are provided with a system that simulates the glenoid cavity.

The articulator may be personalized by adapting the mechanism that simulates the articulations to determined movements that the condyles perform in the glenoid cavity.

Those movements, that are called condylar distances and shown like the edge or limit within which the functional movements of the mandible are performed, may be realized by means of extra-oral or intra-oral registrations.

The extra-oral registrations make use of a pantograph system that is placed onto the face and is blocked onto the mandible and the jaw, and by means of printers, lay-outs are obtained that are transferred onto adaptable articulators that are compatible with this kind of registration.

For what concerns the intra-oral registrations, waxes are used that are indented by the mandible when the latter gets from a central position to a lateral-projecting one. Wax indentations will be performed first on one side and then on the other side. The distance that must be covered by the condyle from the central to the lateral-projecting position is transferred onto adaptable articulators in the mechanism simulating the articulations.

After having obtained the chalk casting (models) of the two arches, the use process may be described as follows:

1. the upper model is plastered, in a correct position, onto the upper branch of the articulator by means of an appropriate instrument (transfer facial arch);
2. once the articulator has been turned upside-down, the upper model will be incuspidated to the lower one that will be plastered to the lower branch;
3. with thermoplastic material a base will be prepared, on the upper model, that covers part of the palate and of the occlusion surface limited to the molar and premolar teeth; this base will be realized in double copy;
4. a plurality of wax thicknesses are made to adhere on the two sides of the occlusion surface of the bases; the softened wax registers the lateral-projecting indenting;
5. once the base has been placed onto the palate, in the mouth the lateral-projecting positions of the mandible will be registered, e.g., first from right to left and then from left to right.

Now the intra-oral registration considers only two positions of the condyles inside the glenoid cavity:

A) the first position is when the mandible is centrated in occlusion; the condyles are placed at the center of the glenoid cavity;
B) the second position is when the mandible is laterally-projecting; from the side of the lateral projection, the condyle is placed forewardly on the bottom and inside moves of about 1.00 cm, while on the other side, it is placed upward and backward of 0.1 to 0.2 cm.

From the ideal union between the two condylar positions—the central one and the lateral-projecting one—the condylar distance is obtained.

As the distance covered by the condyle in its lateral-projecting movement takes place in three dimensions, the mechanical system that simulates the glenoid cavity rotates simultaneously around the transversal axis realizing an inclination from top to bottom and from back to front, together with an inclination that rotates around the vertical axis with an inclination to the inside, from back to front.

These distances may be quantified in grades; on the sagittal plane the inclination of the condylar distance may be registered toward the bottom, and on the horizontal plane the inward deviation of the condyle will be registered.

The transferring of the extra-oral and intra-oral registrations is really very difficult when passing from the mouth to the articulator, and therfore, compromises must be accepted when the mechanical parts are adapted to the condylar distances.

Even if the fundamental structures and the difficulties are the same, criticisms are mainly turned to the adaptable articulators with intra-oral registration with the purposes of showing the needs being the base of the present invention.

All articulators are composed of an upper part and a lower part; the latter shows the mandible.

That part of the articulator showing the mandible consists in turn of a horizontal branch and two vertical branches, like the vertical branches of the mandible.

Their feature is the one of being fixely jointed, like in nature, to the horizontal branch.

This immobility is partially corrected in some articulators in which the vertical branches may perform, along a well delimited transversal axis, only a translatory movement toward the inside or the outside according to the intercondylar distance that is calculated in average about 11.00 cm.

As the mandible is more or less great, a greater or smaller intercondylar distance may be transferred in some articulators by means of facial measurings or by means of the lateral movement.

Furthermore, such measurings appear to be non relevant for the purpose of obtaining a better adaptation of the articulator to the condylar distance. In fact, the mandible moves onto immediate centers that will never intersect with the condyles.

The most relevant need is the one of obtaining an exact relevation of the lateral-projecting position of the mandible from the mouth to the articulator.

When the wax that has registered the lateral-projecting position of the mandible, is transferred from the mouth to the articulator, the immobility of the vertical branches does not allow a monolateral registration, but always includes the two mechanisms that disturb and influence one another.

Practically, once the chalk models have been placed in the two arches of the articulator and the lateral-projection has been registered in the mouth on one side, 1. the base with the registration wax will be moved from the mouth to the upper model;
2. once the mechanisms showing the articulations have been loosened, the chalk model of the lower arch will be indented to the wax registered in the mouth.

This operation appears to be very difficult because the registration of the condylar distance of the side where the condyle moves frontwardly, downwardly and inwardly is disturbed by the contemporary movement toward the top of the counter-lateral condyle.

As the two condylar distances may not be registered at the same time, the indentation of the registered wax on the side of the model fixed in the articulator, implies forcings that constrain and deform the wax forcing the operator to accept compromises.

A further serious inconvenience consists in that the mechanical elements of the articulations do not get automatically adapted to the registered condylar distance, but must be guided and corrected by the operator, which means that where oscillations are noted, the registration of the condylar distance is completely distorted.

SUMMARY OF THE INVENTION

It is the aim of the present invention to completely solve all above mentioned inconveniences of the articulators actually known, by means of an articulating device with an automatic adaptation to the registered condylar distance, divided in three parts integrating one with the others and simulating the upper, the lower and the two vertical branches and that will allow the insertion of the vertical branch onto the lower branch, from front to back, so as to be able to perform the registration of the condylar distance one side after the other without the encumbersome mechanism simulating the temple-mandible articulation of the opposite side.

BRIEF DESCRIPTION OF THE INVENTION

The present invention will be described in more detail hereinbelow relating to the enclosed drawings in which a preferred embodiment is shown.

FIG. 3 shows the details of an embodiment of the articulator device according to the present invention before the vertical branches are placed in site; and FIG. 4 shows an intermediate situation of the utilization process, with the placing in site of the vertical branches.

DETAILED DESCRIPTION OF THE INVENTION

Figure 1:
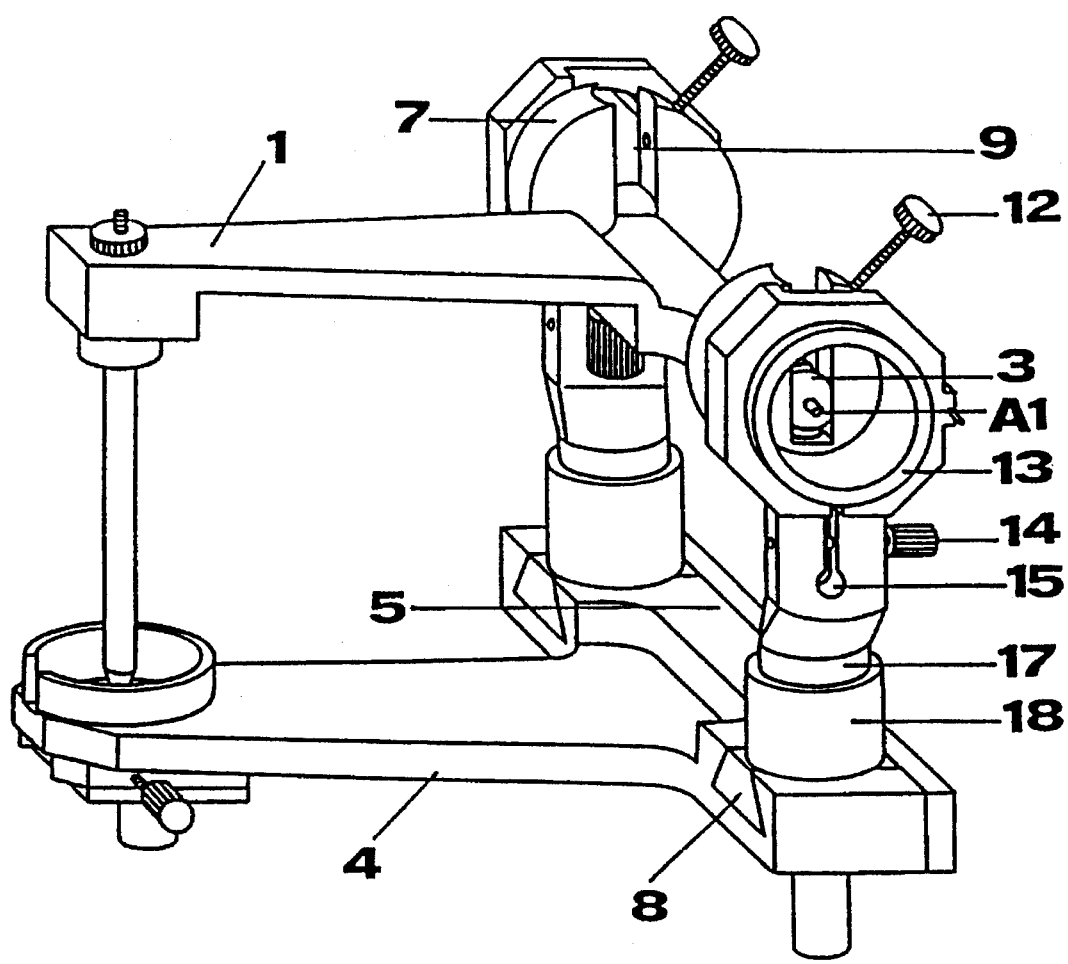
FIG. 1 shows a perspective view of an articulating device with automatic adaptation according to the present invention.
Figure 2:
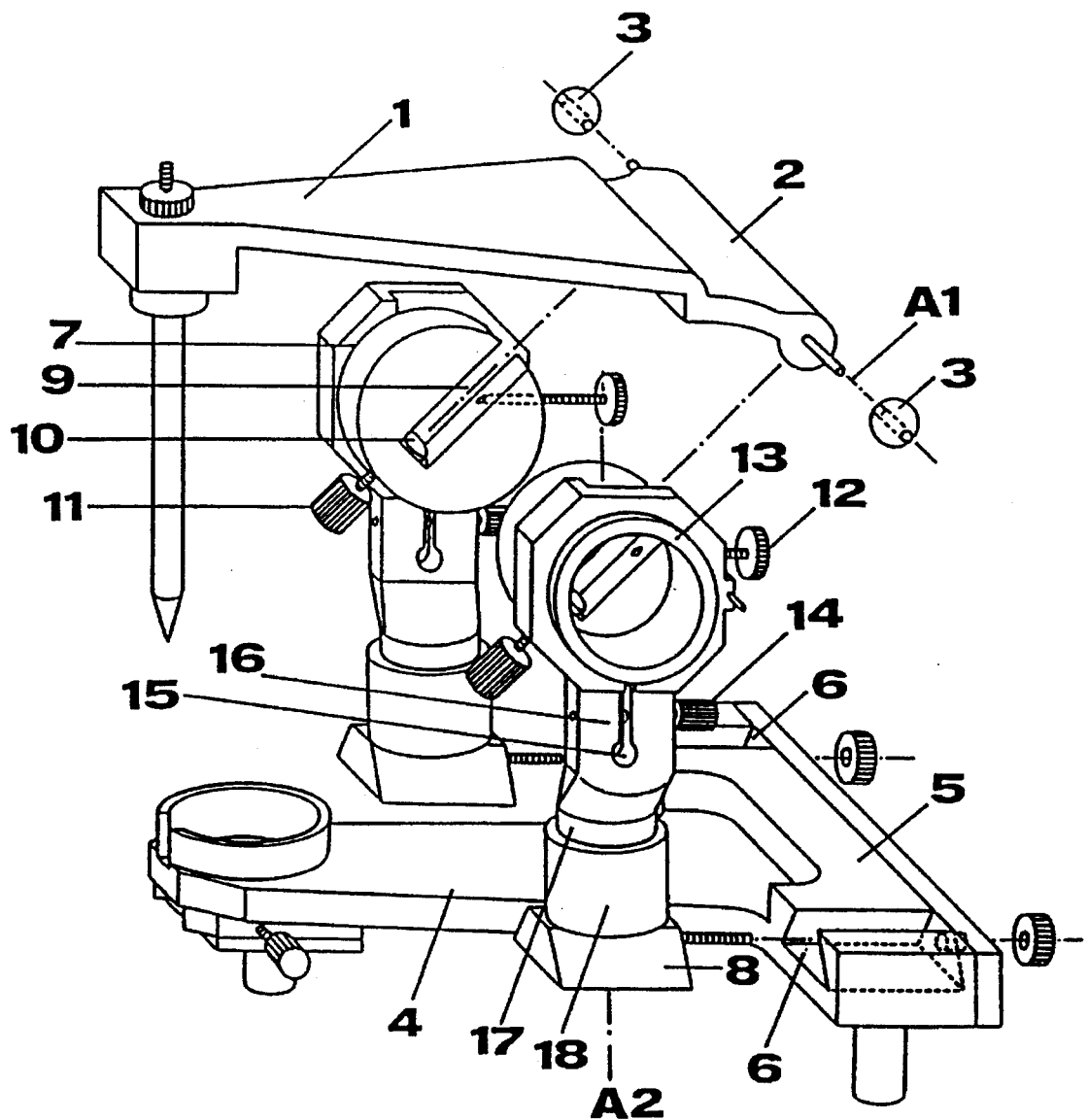
FIG. 2 shows an exploded view of the components of the device according to the present invention.

The enclosed figures show an articulator device with automatic adaptation according to the present invention, mainly consisting of three parts:

an upper branch 1, horizontally placed, T-shaped and provided at the two ends with the transversal axis 2, and small balls 3 that simulate the condyle;

a lower (mandibular) branch 4 having a shape similar to the shape of the upper one, provided at the ends with transversal element 5, with two undercut cavities 6, one for each side, that allow the separate insertion, from front to back and vice versa, of the vertical branches; the cavities 6 are placed in such a way as to propose the intercondylar distance of 11.00 cm;

two vertical branches 7 that, at their top, have a mechanism simulating glenoid cavities, that may be adjusted with rotating movements around transversal axis A1 as well as around vertical axis A2; the base of the branches 7 has a shape 8 so as to allow exact insertion in into the cavities 6 of the lower branch 4.

In particular, the possible adjustings of the articulator according to the present invention may be described as follows:

small balls 3 may slide in grooves 9 and be blocked by rest 10 with a screw pin 11, and by pin 12;

the upper end 13 of the vertical branches 7 may rotate around the transversal axis A1 and be blocked, by striction, by means of a pin 14 operating on the fissure 15 of element 16 surrounding the element 13;

the end 17 of element 7 allows the rotation for adjusting around the vertical axis A2, of the whole upper part of the vertical branches 7 with respect to the cylindrical structure 18, out of one piece with the shapes 8.

For what concerns the functioning of the device according to the present invention, once the indenting of the wax in lateral-projection is obtained the latter will be brought back, with its base, onto the mandible model M already inserted in the lower branch 4 of the articulator.

The indenting of the wax onto the lower model may be soft and delicate because there is no more obstacle to the positioning thereof.

Once the indenting has been fixed by means of glue wax onto the lower model, model M1 already fixed onto the upper branch 1, will be inserted onto the base, so that the two condylar balls 3 may orientate on one side backward, upward and outward, and on the other side, proportionally, frontward and downward (exactly the contrary with respect to what occurs in nature, in the mechanical system, the anatomical relationship between the condyles and the glenoid cavity is turned upside-down). Therefore, while the ball 3 of the upper branch 1 is inserted in the rotating seat 9 of the vertical branch, the vertical branch, with a movement from front to back is inserted and blocked on the base of the lower branch 4.

The mechanical system of the temple-mandible articulations may automatically register the condylar distance on the sagittal plane as well as on the horizontal plane, and may be blocked and kept in this position.

If the registered vertical branch 7 is removed, the same operation may be performed on the other side.

The registered vertical branches 7, transferred onto the horizontal upper branch 1 and lower branch 4, form a personalized device of highest precision and perfectly working.

Beyond those already described, the device according to the present invention shows further advantages:

due to the precision requested in the realization of a prothesis, the articulator adapted to one patient may not be used contemporarily for another patient; therefore, a plurality of instruments must be used. With the articulator according to the present invention, the two horizontal branches are sufficient for housing, each time, any number of personalized vertical branches. Work and money are saved;

it is not necessary to sent a complete articulator from the studio to the laboratory, but only the chalk models and the registered vertical branches, if the laboratory also is provided with the two horizontal branches.

I claim:

1. An articulating device with automatic adaptation, comprising:

an upper branch, wherein a transversal axis is defined between opposite ends of the upper branch, and wherein a first ball and a second ball are provided along the transversal axis for simulating condyles;

a lower branch including a transversal element at one end thereof, wherein the transversal element defines a first undercut cavity at a first side of the transversal element and a second undercut cavity at a second side of the transversal element, wherein the first and second undercut cavities are located so as to simulate an intercondylar distance;

a first vertical branch extending between the upper branch and the lower branch, and a second vertical branch extending between the upper branch and the lower branch, wherein the first vertical branch is placed in the first undercut cavity, and the second vertical branch is placed in the second undercut cavity, wherein the first and second undercut cavities are oriented so as to allow separate insertion of the first and second vertical branches, respectively, wherein a top of the first vertical branch includes a first mechanism for simulating a glenoid cavity and a top of the second vertical branch includes a second mechanism for simulating a glenoid cavity, wherein the first mechanism is adjustable about the transversal axis and about a first vertical axis and the second mechanism is adjustable about the transversal axis and about a second vertical axis, wherein the first mechanism of the first vertical branch is rotatable around the transversal axis, and may be blocked, by striction, by means of a first pin extending into a first fissure of the first vertical branch, and wherein the second mechanism of the second vertical branch is rotatable around the transversal axis, and may be blocked, by striction, by means of a second pin extending into a second fissure of the second vertical branch.

2. An articulating device according to claim 1, wherein the first vertical branch includes a first base which has a shape so as to allow insertion of the first base into the first undercut cavity, and the second vertical branch includes a second base which has a shape so as to allow insertion of the second base into the second undercut cavity.

3. An articulating device according to claim 2, wherein the first base of the first vertical branch is inserted into the first undercut cavity from a front of the transversal element.

4. An articulating device according to claim 3, wherein the second base of the second vertical branch is inserted into the second undercut cavity from the front of the transversal element.

5. An articulating device according to claim 3, wherein the second base of the second vertical branch is inserted into the second undercut cavity from a back of the transversal element.

6. An articulating device according to claim 2, wherein:

a portion of the first vertical branch is rotatable about the first vertical axis with respect to the first base; and a portion of the second vertical branch is rotatable about the second vertical axis with respect to the second base.

7. An articulating device according to claim 2, wherein the first base of the first vertical branch is inserted into the first undercut cavity from a back of the transversal element.

8. An articulating device according to claim 7, wherein the second base of the second vertical branch is inserted into the second undercut cavity from a front of the transversal element.

9. An articulating device according to claim 7, wherein the second base of the second vertical branch is inserted into the second undercut cavity from the back of the transversal element.

10. An articulating device according to claim 1, wherein the first vertical branch is placed in the first undercut cavity from a front of the transversal element.

11. An articulating device according to claim 10, wherein the second vertical branch is placed in the second undercut cavity from the front of the transversal element.

12. An articulating device according to claim 10, wherein the second vertical branch is placed in the second undercut cavity from a back of the transversal element.

13. An articulating device according to claim 1, wherein the first vertical branch is placed in the first undercut cavity from a back of the transversal element.

14. An articulating device according to claim 13, wherein the second vertical branch is placed in the second undercut cavity from a front of the transversal element.

15. An articulating device according to claim 13, wherein the second vertical branch is placed in the second undercut cavity from the back of the transversal element.

16. An articulating device according to claim 1, wherein:

the first ball is slidably received in a first groove defined in the first vertical branch, and the first ball is blocked by a first rest and by a third pin; and the second ball is slidably received in a second groove defined in the second vertical branch, and the second ball is blocked by a second rest and by a fourth pin.

* * * * *